US005567365A

United States Patent [19]
Weinschenk, III et al.

[11] Patent Number: 5,567,365
[45] Date of Patent: Oct. 22, 1996

[54] METHOD OF PRODUCING REPOSITIONABLE INTRAOCULAR LENSES

[75] Inventors: Joseph I. Weinschenk, III, Laguna Niguel; Jim Deacon, Capistrano Beach; Glenn R. Sussman, Lake Forest, all of Calif.

[73] Assignee: Allergan, Inc., Irvine, Calif.

[21] Appl. No.: 249,402

[22] Filed: May 26, 1994

Related U.S. Application Data

[63] Continuation-in-part of Ser. No. 77,810, Jun. 14, 1993.

[51] Int. Cl.$^6$ ........................................ B29D 11/00
[52] U.S. Cl. ................ 264/1.7; 264/2.6; 264/2.7; 264/162; 264/230; 623/6
[58] Field of Search ................ 264/1.7, 2.7, 2.6, 264/230, 162; 623/6

[56] References Cited

U.S. PATENT DOCUMENTS

| | | |
|---|---|---|
| 4,134,161 | 1/1979 | Bayers . |
| 4,136,466 | 1/1979 | Wrue . |
| 4,219,721 | 8/1980 | Kamen et al. . |
| 4,403,354 | 9/1983 | Rainin . |
| 4,435,855 | 3/1984 | Parru . |
| 4,443,441 | 4/1984 | Galin . |
| 4,575,373 | 3/1986 | Johnson . |
| 4,617,023 | 10/1986 | Peyman . |
| 4,642,113 | 2/1987 | Dubroff . |
| 4,661,109 | 4/1987 | White . |
| 4,662,882 | 5/1987 | Hoffer . |
| 4,666,445 | 5/1987 | Tillay . |
| 4,676,793 | 6/1987 | Bechert, II . |
| 4,681,585 | 7/1987 | Sayano et al. . |
| 4,685,921 | 8/1987 | Peyman . |
| 4,685,922 | 8/1987 | Peyman . |
| 4,687,485 | 8/1987 | Lim et al. . |
| 4,781,718 | 11/1988 | Lindstrom . |
| 4,834,753 | 5/1989 | Sulc et al. . |
| 4,872,876 | 10/1989 | Smith . |
| 4,946,470 | 8/1990 | Sulc et al. . |
| 5,108,429 | 4/1992 | Wiley . |
| 5,147,395 | 9/1992 | Willis . |
| 5,217,491 | 6/1993 | Vanderbilt ........................ 264/1.7 |
| 5,259,813 | 12/1993 | Yoshida et al. . |
| 5,288,293 | 2/1994 | O'Donnell, Jr. . |

FOREIGN PATENT DOCUMENTS

| | | |
|---|---|---|
| 0094158 | 11/1983 | European Pat. Off. . |
| 0278724 | 8/1988 | European Pat. Off. . |
| 0336318 | 10/1989 | European Pat. Off. . |
| 0478929 | 4/1992 | European Pat. Off. . |
| 1424828 | 9/1988 | U.S.S.R. . |
| 8701931 | 4/1987 | WIPO . |
| 2007914 | 7/1990 | WIPO . |

OTHER PUBLICATIONS

Friedberg et al, Arch Ophthalmol, Mar. 1992, 110 (3) pp. 413–415.
Chan, Ophthalmology, Jan. 1992, 99 (1) pp. 51–57.
Bowman et al, J. Cataract Refract. Sur., Nov. 1991, 17 (6) pp. 843–847.
Flynn et al, J. Cataract Refract. Surg., Jan. 1990, 16 (1) pp. 51–56.
Smiddy, Arch Ophthalmol., Nov. 1989, 107 (11) pp. 1678–1680.
Neumann et al, J. Cataract Refrct. Surg., Nov. 1987, 13 (6) pp. 653–656.

(List continued on next page.)

*Primary Examiner*—Mathieu D. Vargot
*Attorney, Agent, or Firm*—Frank J. Uxa

[57] ABSTRACT

Methods for producing intraocular lenses which can be non-surgically repositioned after being placed in an eye. Such methods include providing a lens blank at least a portion of which is a polymeric material having a glass transition temperature of at least about 40° C., and forming from the lens blank an intraocular lens including an optic and a fixation member so that at least a portion of the fixation member is made of the polymeric material. The position of the optic in the eye can be changed by heating the fixation member to a temperature above the glass transition temperature.

20 Claims, 1 Drawing Sheet

OTHER PUBLICATIONS

Stark et al, Ophthalmic Surg., Aug. 1980, 11 (8) pp. 495–497.

Poley et al, J. Am. Intraocular Implant Soc., Oct. 1979, 5 (4) pp. 316–320.

Praeger, Ophthalmic Surg., Jul. 1979, 10 (7) pp. 30–32.

Corcoran, J. Am. Intraocular Implant Soc., Nov. 1985, 11 (6) pp. 598–599.

Moretsky, J. Am. Intraocular Implant. Soc., 1984, 10 (4) pp. 477–480.

Wand et al, Surg. Ophthalmol., 1980, 25 (2) pp. 75–84.

Flynn, Graefes Arch. Clin. Exp. Ophthalmol, 1987, 225 (3) pp. 169–172.

Nevyas et al., J. Cataract Refract. Surg., Mar. 1987, 13 (2) pp. 201–204.

Sternberg et al, Arch. Ophthalmol, Sep. 1986, 104 (9) pp. 1391–1393.

Ayaki et al, Nippon Ganka Gakkai Zasshi, Jun. 1990, 94 (6) pp. 553–558 (I).

Lyons et al, J. Cataract Refract. Surg., Jul. 1990 16 (4) pp. 509–511.

Nabors et al, Ophthalmic Surg., Apr. 1990, 21 (4) pp. 263–265.

Smiddy et al, Ophthalmology, Jun. 1991, 98 (6) pp. 889–894.

Bloom et al, Ophthalmic Surg., Dec. 1990, 21 (12) pp. 851–854.

Ayaki et al, Nippon Ganka Gakkai Zasshi, Jun. 1990, 94 (6) pp. 559–565.

Biedner et al, Am. J. Opthalmol, Aug. 1977, 84 (2) p. 265.

U.S. Patent     Oct. 22, 1996     5,567,365
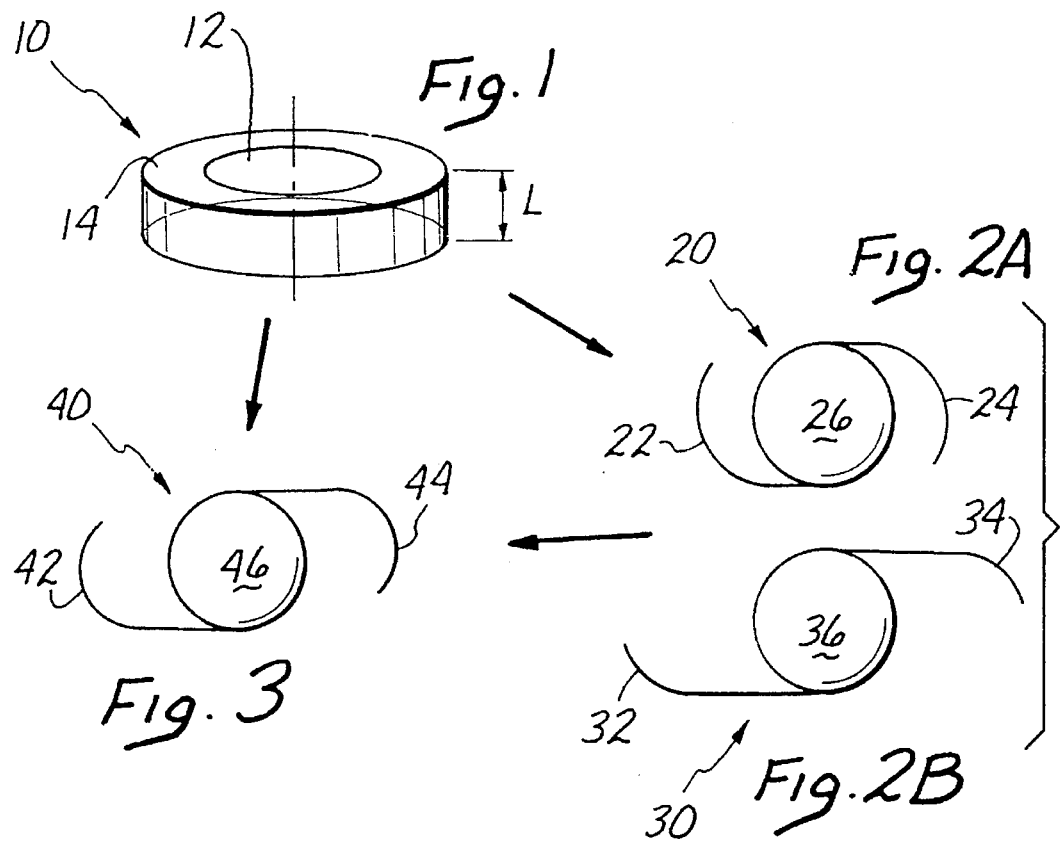
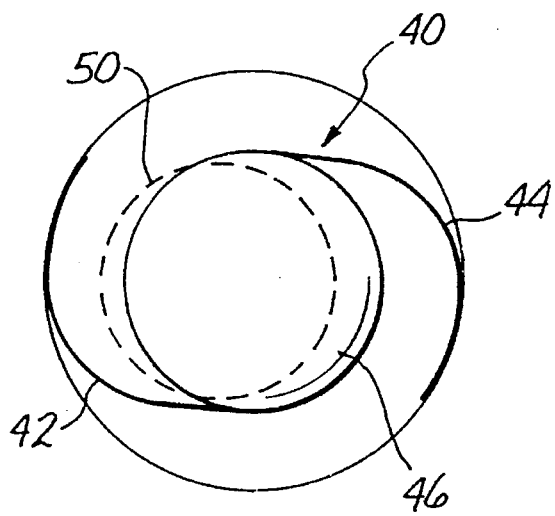
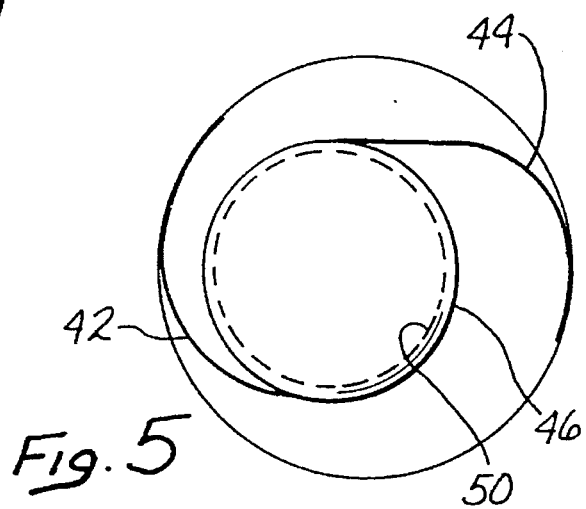

METHOD OF PRODUCING REPOSITIONABLE INTRAOCULAR LENSES

RELATED APPLICATION

This application is a continuation-in-part of application Ser. No. 08/077,810, filed Jun. 14, 1993. The disclosure of this prior application is incorporated herein in its entirety by reference.

BACKGROUND OF THE INVENTION

This invention relates to methods of producing intraocular lenses (IOLs), in particular to methods for producing IOLs structured to be repositioned after being placed in an eye.

The vision impairing disease, known as cataract, can be alleviated by surgically replacing the natural lens of the eye with an artificial IOL. Such an IOL may be inserted in the eye by a variety of well known surgical procedures. However, once the IOL is placed in the eye, it is often found that the IOL optic is or becomes decentered or otherwise moves to a less-than-optimal position in the eye.

IOLs, for example, IOLs located in the anterior chamber or posterior chamber of the eye, which are not optimally positioned in the eye or centered on the visual axis of the eye are prone to a variety of optical and physical problems, such as optical distortion, edge glare, second images, reduction in multifocal effect (in some designs) and the like. In addition, posterior chamber opacification may be altered or encouraged by a decentered IOL. Decentration has been reduced by use of continuous capsulorhexis techniques and bag placement, but has not been eliminated. Further, the smaller diameter IOL optics increasingly used today tend to require more precise positioning and to be more sensitive to relatively minor amounts of mal-positioning than their larger diameter predecessors. Even a perfectly positioned IOL may move slightly as remnant lens epithelial cells fill in the capsule.

Repositioning an IOL by mechanical means after IOL implantation is an invasive procedure involving reopening the eye and working behind the iris. In extreme cases, IOL removal may be indicated. Aside from the disadvantages of the surgical procedure itself, possible further complications include inflammation, infection, pigmentary dispersion and endothelial damage.

It would be advantageous to provide methods for producing IOLs that can be repositioned after being placed in the eye without requiring such invasive surgical techniques.

SUMMARY OF THE INVENTION

Methods for producing IOLs structured to be post-operatively repositioned have been discovered. The present IOLs are repositionable, that is are structured to allow repositioning in the eye, for example, in the coronal plane, by the use of energy, such as heat energy, passed into the eye, for example, through the pupil of the eye, and/or by the use of one or more other non-invasive techniques.

The present IOL production methods provide IOLs which have controlled chemical make-ups and structures so that the IOLs can be predictably moved or repositioned in the eye in a non-surgical manner. The present methods employ materials which are responsive to changes in temperature above that present in the eye to alter the configuration of the IOL in the eye. In addition, the present methods can employ conventional and straightforward IOL-forming techniques and procedures, such as machining, e.g., lathing, in producing the presently useful IOLs. The present methods are very effective in producing IOLs with small diameter optics. Manufacturing costs, IOL implantation procedures, etc. are substantially equivalent to current IOLs and procedures. In short, the present IOL production methods are very effective and convenient for producing IOLs which are readily and controllably repositionable after being placed in the eye in a substantially non-invasive manner. This non-invasive approach to repositioning an IOL allows the surgeon to properly position the IOL optic, for example, center the optic relative to the pupil or to the optical or visual axis, in the eye either immediately following surgery or later, as desired or required.

In one broad aspect, the present invention is directed to methods for producing an IOL which comprise: providing a lens blank, at least a portion of which comprises a polymeric material having a glass transition temperature of at least about 40° C.; and forming from this lens blank an IOL including an optic and a fixation member so that at least a portion of the fixation member is made of the polymeric material. The IOL formed preferably includes a plurality of such fixation members.

The optic of the present IOLs functions in a manner similar to a conventional optic of a conventional IOL. Similarly, the fixation member or members (haptics) of the present IOLs function in a manner similar to a fixation member or haptic of a conventional IOL. In the presently formed IOLs the fixation member or members are alterable, that is the fixation member or members have configurations capable of being altered, preferably non-surgically altered, after the IOL is placed in an eye to at least assist in repositioning, preferably controllably repositioning, the optic in the eye. The fixation member or members can have any suitable configuration provided that such member or members are alterable as described herein.

The present methods produce IOLs which are repositionable in the eye to allow the optic to be moved in a manner, preferably in a substantially predictable and more preferably a substantially predetermined manner, to provide substantial control of the positioning of the IOL in the eye. In one particularly useful embodiment, the fixation member of the IOL requiring repositioning in the eye is exposed through the pupil of the eye. When sufficient repositioning of the optic has been achieved, this fixation member no longer is exposed through the pupil so that the repositioning is self-limiting and relatively fail-safe.

The polymeric materials which make up at least a portion, and preferably substantially all, of the fixation member or members having the above-noted glass transition temperature (Tg), hereinafter referred to as Tg materials, are employed to facilitate repositioning of the optic in the eye, as desired and/or required.

In one embodiment the fixation member (or part thereof) or members made of a Tg material have no specific "memory" based on their manufacturing history. Thus, by heating such a "non-memory" fixation member (or part thereof) while it is under compression in the eye to a temperature above Tg, the fixation member (or part thereof) temporarily softens so that the fixation member is further bent or compressed, moving the optic of the IOL in the eye, preferably in a controlled manner, to reposition the optic in the eye. The heating is preferably ended or stopped so that the optic of the IOL moves or is repositioned only to the extent desired.

In another embodiment, the fixation member (or part thereof) or members made of a Tg material are originally formed to have a shape so as to be unacceptable for use in a human eye. For example, the above-noted forming step can produce a fixation member which has a distal end that extends too far away from the optic to be acceptable for use in the eye or which has a distal end that is too close to the optic to be acceptable for use in a human eye. In this embodiment, the present methods further comprise heating at least a portion of the fixation member or members above the Tg of the Tg material, altering the shape of the heated fixation member or members, preferably to a shape in which the fixation member or members are acceptable for use in a human eye, and cooling the heated fixation member or members to a temperature below the Tg of the Tg material while maintaining the fixation member or members in the altered shape. After such an IOL is implanted in an eye, the fixation member (or part thereof) can be heated to a temperature above Tg. When this happens, the fixation member seeks to return to its original shape and, in so doing, moves the optic, preferably in a controlled manner, so as to reposition the optic. The heating is preferably ended or stopped so that the optic of the IOL moves or is repositioned only to the extent desired.

The fixation member (or part thereof) in the eye may be heated to a temperature above the Tg of the Tg material in any suitable manner, for example, by passing radiant energy into the eye, such as through the pupil of the eye. Radiant energy can be passed into the eye, for example, from a thin probe tip passed into the eye through a "pin-size" incision having a size of no more than about 0.2 mm and positioned immediately adjacent or in contact with the fixation member (or part thereof) to be heated.

The lens blank includes a material from which the optic of the IOL is produced. Any suitable material may be employed provided that it can be formed into a functional and effective IOL optic. Materials conventionally employed in IOL optics may be employed. Examples of materials from which the optics of the presently produced IOLs can be formed include silicon-based polymer materials, such as polysiloxane-based elastomeric materials, acrylic-based polymer materials, such as polymethylmethacrylate (PMMA) and the like, hydrogel-forming polymer materials, other polymer materials, glass and the like and mixtures thereof. The lens blank preferably includes a material, preferably a polymer material, other than the above-noted Tg material, and the forming step results in an optic comprising this other material.

Any suitable polymeric material having a Tg of at least about 40° C. or about 45° C., preferably in the range of about 40° C. to about 80° C. and more preferably in the range of about 45° C. to about 60° C., can be used in the present methods to produce IOLs. The material should be such that the Tg is sufficiently high to avoid any changes in the configuration of the fixation member or members caused by the physiological environment within the eye. On the other hand, the Tg of the Tg material should not be excessively high, since heating the fixation member (or part thereof) to such high temperatures may cause harm or damage to the eye exposed to such temperatures. Typical examples of useful Tg materials from which the fixation member (or part thereof) or members are derived include homopolymers of and copolymers derived from ethyl methacrylate, 3,3-dimethylbutyl methacrylate, isobutyl methacrylate, cyclohexyl methacrylate, sec-butyl methacrylate, benzyl methacrylate, 4-tert-butylphenyl acrylate, 4-ethoxycarbonyl phenyl acrylate, 2-methoxycarbonyl phenyl acrylate, 3-methoxycarbonyl phenyl acrylate, 4-methoxycarbonyl phenyl acrylate, phenyl acrylate and the like and mixtures thereof. Polymers other than acrylic-based materials, such as certain acrylamides, polyolefins, polycarbonates and the like may be useful as Tg materials in the present invention. Copolymers are particularly useful as Tg materials since such copolymers can be custom formulated to obtain the specific Tg and other properties desired.

In one embodiment, the above-noted providing step comprises producing a rod comprising an elongated core and an outer layer surrounding the elongated core along the length of the elongated core. The outer layer comprises the Tg material. This composite rod is divided, for example, cut, into pieces, to form lens blanks each of which comprises a portion of the elongated core surrounded around its length by a portion of the outer layer. In this embodiment, the forming step preferably comprises deriving the optic from the portion of the elongated core making up the lens blank and deriving the fixation member or members from the portion of the outer layer making up the lens blank.

In another embodiment, the above-noted providing step comprises producing a lens blank comprising a core portion having a length and an outer layer portion surrounding the core portion along the length of the core portion. In this embodiment, the forming step comprises deriving the optic from the core portion and deriving the fixation member or members from the outer layer portion.

The elongated core or core portion is preferably produced by polymerizing a polymerizable component. The producing step preferably further comprises polymerizing another polymerizable component, other than the polymerizable component noted above, to yield the outer layer. The polymerizable component or components may be chosen from monomers or combinations of monomers which, upon or after polymerization, yield the desired polymeric materials or polymer materials. Such polymerizable component or components may be conventional and well known in the art. In a particularly useful embodiment, the polymerizable components are chosen so that the polymer material and polymeric material are substantially compatible. This compatibility may be obtained, for example, using similar type materials, such as acrylic-type materials, for both the polymer material and the polymeric material. Such compatibility is preferably sufficient so that an interpenetrating network forms at or near the interface of the polymer material and polymeric material so that such materials are securely bonded together.

The conditions at which the above-noted polymerization or polymerizations occur may be conventional and well known in the art. The polymerizable component or components are chosen so as to yield, upon or after polymerization, the desired polymeric and polymer materials. The polymerization conditions are chosen to be effective to facilitate the polymerization of the polymerizable component or components.

In a particularly useful embodiment, the material, preferably polymer material, or precursor material, for the optic, or the optic and part of the fixation member or members, of the final IOL is cast and formed as either an elongated core or a core portion. Then the Tg material or precursor for this Tg material is cast around and along the length of the elongated core or core portion and formed as either an outer layer of an elongated rod or an outer layer portion of an individual lens blank. If an elongated rod is produced, it is divided, e.g., cut, into lens blanks or buttons. The lens blanks thus produced are then machined, for example, lathed, in a conventional manner to produce a final IOL or an IOL precursor, which precursor is then processed, as described herein, to produce a final IOL.

In another aspect of the invention, methods for producing an IOL and repositioning the IOL in the eye are provided. The IOL is produced in a manner substantially as set forth elsewhere herein. This IOL is then placed in an eye, preferably using conventional and well-known IOL implantation techniques. The IOL in the eye is repositioned, preferably non-surgically repositioned, by heating at least a portion of one of the fixation members in the eye to a temperature above the Tg of the Tg material for a sufficient period of time to alter the configuration of the fixation member and to move, preferably controllably move, the optic in the eye.

As used herein, the term "non-surgically" means that the IOL is repositioned without requiring a conventionally sized surgical incision, such as an incision having a size of greater than about 0.5 mm and/or without being physically contacted, that is grasped and/or pushed and/or pulled, by any mechanical device, such as a conventional knife and/or other mechanical surgical instrument. In the event an incision in the eye is made to facilitate the IOL repositioning in accordance with the present invention, it is preferred that such incision have a size of about 0.5 mm or less than about 1 mm. Incisions of this size are substantially smaller than those conventionally required to surgically reposition IOLs, cause little or no trauma and require little or no healing time before the patient can conduct or perform normal activity.

The invention, together with additional features and advantages thereof, may best be understood with reference to the following description made in connection with the accompanied illustrated drawing.

BRIEF DESCRIPTION OF THE DRAWINGS

FIG. 1 is a top front view, in perspective, of a lens blank used in accordance with the present invention.

FIG. 2A is a top plan view of one embodiment of an IOL precursor formed from the lens blank shown in FIG. 1.

FIG. 2B is a top plan view of another embodiment of an IOL precursor formed from the lens blank shown in FIG. 1.

FIG. 3 is a top plan view of an IOL derived from the lens blank shown in FIG. 1.

FIG. 4 is a schematic illustration of an IOL produced in accordance with the present invention decentered relative to the pupil of an eye.

FIG. 5 is a schematic illustration of the IOL shown in FIG. 4 after its configuration has been altered, showing such altered IOL to be properly centered relative to the pupil of the eye.

DETAILED DESCRIPTION OF THE INVENTION

FIG. 1 illustrates a lens blank, shown generally at 10, which is provided and from which an IOL 40 (FIG. 3) is derived. Lens blank 10 includes a core 12 and an outer layer 14 which surrounds the core along the length L of the lens blank. Lens blank 10 is prepared by casting an optically clear polymer material into the shape of core 12. A particularly useful material for core 12 is PMMA. The optic 46 and the proximal portions of fixation members 42 and 44 of IOL 40 (FIG. 3) are derived from core 12. A polymeric material having a Tg of about 45° C., such as poly (3,3-dimethylbutyl methacrylate) is cast in the shape of outer layer 14 around core 12. The distal portions of fixation members 42 and 44 of IOL 40 are made from outer layer 14.

It should be noted that lens blank 10 can be provided in any suitable manner. For example, individual lens blanks, such as lens blank 10, can be produced by separately forming the core 12 and then forming the outer layer 14 around the pre-formed core 12. The forming of core 12 can be achieved by polymerizing a polymerizable component, that is one or more monomeric components and, possibly, other components to produce the core. Once the core is formed, it can be placed in a mold and surrounded by another polymerizable component or polymer precursor, that is one or more monomeric components, and, possibly, additional materials. This polymer precursor surrounding the pre-formed core is polymerized to produce the outer layer 14.

As an alternate for providing lens blank 10, an elongated composite rod can be produced. This elongated rod contains an elongated core surrounded along its length by an elongated outer layer. This elongated core and elongated outer layer can be produced in a manner similar to the manner described above for producing the core 12 and outer layer 14 of lens blank 10. Once the elongated rod is produced, it can be cut in a direction transverse to the longitudinal axis of the elongated rod to produce a multiplicity of lens blanks, such as lens blank 10.

The polymerization of the various polymerizable components noted above and the selection of the individual polymerizable components can be accomplished using conventional techniques. Therefore, such techniques are not described in detail herein.

One important aspect of the present invention is that the outer layer of the lens blank be formed, at least in part, from a polymeric material having a Tg of at least about 40° C. or about 45° C., more preferably in the range of about 45° C. to about 60° C. Of course, the polymeric material (as well as the material from which the optic is derived) used should be compatible with the eye so that implantation of the final IOL does not cause any significant harm or damage to the eye.

In addition, the core 12 of the lens blank 10 should be made of an optically clear material which is suitable in IOL optics. Again, such material should be compatible with the eye in which the IOL produced in part from the core 12 is implanted.

Once lens blank 10 is provided, it is machined into an IOL precursor, such as shown in FIGS. 2A and 2B or directly into an IOL, such as shown in FIG. 3. This machining can occur using conventional automated lens forming machinery, for example, an automatic lathe.

The IOL precursors shown in FIGS. 2A and 2B are configured to be unacceptable for implantation into a human eye. Thus, the IOL precursor 20 shown in FIG. 2A includes diametrically opposed fixation members 22 and 24 the distal ends of which are located too close to the optic 26 to be acceptable for use in a human eye. The IOL precursor 30 shown in FIG. 2B includes fixation members 32 and 34 the distal ends of which extend too far away from the optic 36 to be acceptable for use in a human eye. Both optics 26 and 36 are derived substantially completely from core 12, while the distal portions of fixation members 22, 24, 32 and 34 are derived from outer layer 14. If desired, the fixation members can be made substantially completely out of the material of outer layer 14. The fixation members 22, 24, 32 and 34 comprise a polymeric material having a glass transition temperature of about 45° C.

After these "unacceptably configured" IOL precursors are produced, the fixation members are heated to above the glass transition temperature and the configuration of the fixation members are altered so as to be acceptable for use in a human eye. Such a configuration is shown in FIG. 3 with IOL 40. After the heated IOL precursors are altered so that the fixation members are configured to be acceptable, the fixation members are cooled below the glass transition temperature while maintaining the fixation members in the altered configuration. At this point, after cooling below Tg, the IOL precursors are configured as shown in FIG. 3. Thus, IOL 40 includes acceptably configured fixation members 42 and 44 and optic 46.

IOL 40 made from either IOL precursor 20 or IOL precursor 30 has a "memory" based on its manufacturing history. Such a "memory" IOL 40 can be effectively used as follows:

Referring now to FIGS. 4 and 5, "memory" IOL 40 can be implanted into a mammalian eye, for example, a human eye, using conventional and well-known surgical techniques, such as techniques which are commonly used to implant conventional IOLs. In general, an incision is made in the eye and a natural lens is removed, for example, using a conventional phacoemulsification procedure. With the lens capsule vacated, the "memory" IOL 40 is introduced into the eye, such as into the posterior chamber of the eye, and is positioned and fixed within the eye. The incision is then repaired. After healing, the "memory" IOL 40 implanted in the eye is effective to provide vision correction to the recipient of the IOL. The present invention is also applicable to IOLs structured for placement within the anterior chamber of the eye. Such anterior chamber IOLs for the production and use of such anterior chamber IOLs are within the scope of the present invention.

The "memory" IOL 40 can be, or over a period of time can become, decentered relative to the pupil of the eye 50 as shown in FIG. 4. If this condition is left as is, "memory" IOL 40 becomes substantially less effective to provide proper vision to the recipient. Optical distortion, glare, and/or other possible problems exist when "memory" IOL 40 is decentered as in FIG. 3.

In general, with a "memory" IOL 40, the fixation member (or part thereof) is heated, for example, by passing radiant energy through the pupil of the eye to heat the fixation member (or part thereof) to a temperature above the Tg to recenter the optic 46. For example, with specific reference to FIG. 2A, fixation members 22 and 24 are originally manufactured in a highly curved configuration. By heating fixation member 42 to above its glass transition temperature, to about 50° C. (by passing radiant energy, for example, from a thin probe tip packed into the eye through a "pin-sized" incision having a size of no more than about 0.2 mm and positioned immediately adjacent or in contact with this part) fixation member 42 moves toward its highly curved configuration, thereby causing optic 46 to move left and to be centered relative to the pupil 50 of the eye.

In the case where "memory" IOL 40 is derived from IOL precursor 30, "memory" IOL is repositioned, for example, in the coronal plain as follows. A pin-sized probe is introduced into the eye adjacent to fixation member 44. The pin-sized probe causes fixation member 44 to be heated to a temperature above the Tg. This causes fixation member 44 to begin to move toward its original configuration as shown in FIG. 2B. This movement of fixation member 44 causes optic 46 to move to the left so that optic 46 is centered around pupil 50, as shown in FIG. 5. Once this repositioning has occurred, the heating is stopped and the pin-sized probe is removed from the eye.

In another embodiment, the fixation members 42 and 44 are made of Tg material which has no specific "memory" based on its manufacturing history (such as the Tg material described in the two immediately preceding paragraphs). In this embodiment, the IOL 40 is made directly from lens blank 10 without any heating and cooling steps as described above.

By heating such a fixation member 42 while it is under compression in the eye to a temperature above Tg, the fixation member (or part thereof) temporarily softens so that the fixation member is further bent or compressed moving the optic 46 of the IOL 40 to the left in the eye. For example, with specific reference to FIG. 4, fixation member 42 is made of such a Tg material. By heating this part to above its glass transition temperature, to about 50° C. (for example, as described above), fixation member 42 temporarily softens thereby causing the fixation member to further bend or compress. This, in turn, causes optic 46 to move left and be centered relative to the pupil 50 of the eye.

While this invention has been described with respect to various specific examples and embodiments, it is to be understood that the invention is not limited thereto and that it can be variously practiced within the scope of the following claims.

What is claimed is:

1. A method of producing an intraocular lens which comprises:

providing a lens blank at least a portion of which comprises a polymeric material having a glass transition temperature in the range of about 40° C. to about 60° C.; and forming from said lens blank an intraocular lens including an optic and a fixation member so that at least a portion of said fixation member is made of said polymeric material, wherein said intraocular lens is formed so as to be repositionable after being placed in an eye by heating said at least a portion of said fixation member in the eye to a temperature above the glass transition temperature of said polymeric material to alter the configuration of said fixation member and move said optic.

2. The method of claim 1 which further comprises, prior to insertion of said intraocular lens in an eye, heating at least a portion of said fixation member above the glass transition temperature of said polymeric material, altering the shape of said heated fixation member and cooling said heated fixation member to a temperature below the glass transition temperature of said polymeric material while maintaining said fixation member in the altered shape.

3. The method of claim 1 wherein said lens blank includes a polymer material other than said polymeric material, and said forming results in said optic comprising said polymer material.

4. The method of claim 1 wherein said polymeric material has a glass transition temperature in the range of about 40° C. to about 45° C.

5. The method of claim 1 wherein said forming step results in said intraocular lens having two of said fixation members.

6. The method of claim 1 wherein said forming step comprises machining said lens blank.

7. The method of claim 1 wherein said forming step comprises lathing said lens blank.

8. The method of claim 1 wherein said providing step comprises:

producing a rod comprising an elongated core and an outer layer surrounding said elongated core along the length of said elongated core, said outer layer comprising said polymeric material; and dividing said rod to form said lens blank which comprises a portion of said elongated rod surrounded along its length by a portion of said outer layer.

9. The method of claim 8 wherein said forming step comprises deriving said optic from said portion of said elongated rod and deriving said fixation member from said portion of said outer layer.

10. The method of claim 1 wherein said providing step comprises:

producing a lens blank comprising a core portion having a length and an outer layer portion surrounding said core portion along the length of said core portion.

11. The method of claim 10 wherein said forming step comprises deriving said optic from said core portion and deriving said fixation member from said outer layer portion.

12. The method of claims 2 wherein said fixation member after said forming step and prior to said heating step is shaped so as to be unacceptable for use in a human eye and is after said cooling step shaped so as to be acceptable for use in a human eye.

13. The method of claim 12 wherein said fixation member after said forming step and prior to said heating step extends too far away from said optic to be acceptable for use in a human eye.

14. The method of claim 12 wherein the distal end of said fixation member after said forming step and prior to said heating step is located too close to said optic to be acceptable for use in a human eye.

15. The method of claim 8 wherein said producing step comprises polymerizing a polymerizable component.

16. The method of claim 8 wherein said producing step comprises polymerizing a first polymerizable component to yield said elongated core and polymerizing a second polymerizable component, other than said first polymerizable component, to yield said outer layer.

17. The method of claim 10 wherein said producing step comprises polymerizing at least one polymerizable component.

18. The method of claim 10 wherein said producing step comprises polymerizing a first polymerizable component to yield said core portion and polymerizing a second polymerizable component, other than said first polymerizable component, to yield said outer layer portion.

19. A method of producing an intraocular lens and repositioning the intraocular lens in an eye comprising:

providing a lens blank at least a portion of which comprises a polymeric material having a glass transition temperature in the range of about 40° C. to about 60° C.;

forming from said lens blank an intraocular lens including an optic and a fixation member so that at least a portion of said fixation member is made of said polymeric material; and, thereafter, placing said intraocular lens in an eye; and non-surgically repositioning said intraocular lens in the eye by heating at least a portion of said fixation member in the eye to a temperature above the glass transition temperature of said polymeric material for a sufficient period of time to alter the configuration of said fixation member and to controllably move said optic in the eye.

20. The method of claim 19 which further comprises, prior to said placing step, heating at least a portion of said fixation member above the glass transition temperature of said polymeric materials, altering the shape of said heated fixation member and cooling said heated fixation member to a temperature below the glass transition temperature of said polymeric material while maintaining said fixation member in the altered shape.

\* \* \* \* \*

UNITED STATES PATENT AND TRADEMARK OFFICE
CERTIFICATE OF CORRECTION

PATENT NO. : 5,567,365
DATED : October 22, 1996
INVENTOR(S) : Weinschenk, III et al It is certified that error appears in the above-indentified patent and that said Letters Patent is hereby corrected as shown below:

The Title should read as follows: --METHODS OF PRODUCING REPOSITIONABLE INTRAOCULAR LENSES--.

Column 6, line 39; delete "Of" and insert in place thereof --of--.

Claim 12, line 16; delete "claims" and insert in place thereof --claim--.

Signed and Sealed this

First Day of December, 1998

*Attest:*

BRUCE LEHMAN

*Attesting Officer*    Commissioner of Patents and Trademarks